United States Patent
Peterson et al.

(10) Patent No.: US 12,115,343 B2
(45) Date of Patent: Oct. 15, 2024

(54) IMPLANTABLE MEDICAL DEVICE WITH DRUG RESERVOIR VOLUME SENSOR SYSTEM

(71) Applicant: Medtronic, Inc., Minneapolis, MN (US)

(72) Inventors: Erik J. Peterson, Fridley, MN (US); Touby A. Drew, Golden Valley, MN (US); Jerel K. Mueller, Saint Paul, MN (US); Sarah J. Offutt, Golden Valley, MN (US); Carl M. Feller, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1051 days.

(21) Appl. No.: 16/948,753

(22) Filed: Sep. 30, 2020

(65) Prior Publication Data
US 2022/0096738 A1    Mar. 31, 2022

(51) Int. Cl.
A61M 5/142    (2006.01)
A61M 5/168    (2006.01)
G01F 17/00    (2006.01)

(52) U.S. Cl.
CPC ...... *A61M 5/14276* (2013.01); *A61M 5/1684* (2013.01); *G01F 17/00* (2013.01); *A61M 2205/18* (2013.01); *A61M 2205/3375* (2013.01); *A61M 2205/3379* (2013.01); *A61M 2205/3389* (2013.01); *A61M 2205/3584* (2013.01); *A61M 2205/52* (2013.01)

(58) Field of Classification Search
CPC ........ A61M 5/1684; A61M 2205/3375; A61M 5/14276
See application file for complete search history.

(56) References Cited

U.S. PATENT DOCUMENTS

| | | |
|---|---|---|
| 4,360,019 A | 11/1982 | Portner et al. |
| 4,573,994 A | 3/1986 | Fischell et al. |
| 4,772,263 A | 9/1988 | Dorman et al. |
| 5,217,442 A | 6/1993 | Davis |
| 6,210,368 B1 * | 4/2001 | Rogers .............. A61M 5/14593 604/131 |

(Continued)

FOREIGN PATENT DOCUMENTS

WO    WO 2013/052414 A2    4/2013

OTHER PUBLICATIONS

Extended European Search Report for European Application No. 19202531.0, dated Jan. 27, 2020.

*Primary Examiner* — Jenna Zhang

(74) *Attorney, Agent, or Firm* — Husch Blackwell LLP

(57) ABSTRACT

An implantable medical device (IMD) includes a drug reservoir located within a reservoir chamber of the IMD that includes a first side and a second side directly opposite the first side defining a reservoir volume there between. The IMD further includes and a volume sensor system including an ultrasound transmitter within the reservoir chamber and positioned to transmit an ultrasound signal toward the second side at an angle relative to the second side and a plurality of ultrasound sensors adjacent to at least one of the first side or second side of the drug reservoir with each sensor positioned to selectively receive the signal from the transmitter at different reservoir volume levels to indicate a current volume capacity of the drug reservoir.

20 Claims, 7 Drawing Sheets

(56) References Cited

U.S. PATENT DOCUMENTS

| | | |
|---|---|---|
| 6,283,943 B1 | 9/2001 | Dy et al. |
| 6,579,280 B1 | 6/2003 | Kovach et al. |
| 6,962,580 B2 | 11/2005 | Adams et al. |
| 7,072,802 B2 | 7/2006 | Hartlaub |
| 7,637,897 B2 | 12/2009 | Ginggen |
| 7,942,863 B2 | 5/2011 | Kalpin et al. |
| 9,122,785 B2 | 9/2015 | Alme et al. |
| 9,421,325 B2 * | 8/2016 | Kalpin ................ G01F 23/14 |
| 11,654,247 B2 * | 5/2023 | Klemm ............. A61M 5/3157 |
| | | 604/506 |
| 2005/0267500 A1 * | 12/2005 | Hassler, Jr. ........... A61F 5/0003 |
| | | 606/157 |
| 2006/0089619 A1 | 4/2006 | Ginggen |
| 2006/0089620 A1 | 4/2006 | Gibson et al. |
| 2007/0255259 A1 * | 11/2007 | Miesel ............. A61M 5/14276 |
| | | 604/890.1 |
| 2008/0243093 A1 | 10/2008 | Kalpin et al. |
| 2011/0301575 A1 | 12/2011 | Miesel et al. |
| 2012/0265141 A1 * | 10/2012 | Kalpin ............... A61M 5/1684 |
| | | 604/131 |
| 2013/0086982 A1 * | 4/2013 | Miesel ................. G01F 17/00 |
| | | 73/149 |
| 2013/0116665 A1 | 5/2013 | Humayun et al. |
| 2014/0228765 A1 | 8/2014 | Burke et al. |
| 2017/0043151 A1 | 2/2017 | Bellrichard et al. |
| 2018/0214635 A1 * | 8/2018 | Raman ................ A61M 5/172 |

* cited by examiner

IMPLANTABLE MEDICAL DEVICE WITH DRUG RESERVOIR VOLUME SENSOR SYSTEM

TECHNICAL FIELD

The present application relates to medical devices that include expandable drug reservoirs and techniques to determine the drug reservoir volume of such devices.

BACKGROUND

A variety of medical devices are used for acute, chronic, or long-term delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, drug infusion pumps or other fluid delivery devices can be used for chronic delivery of therapeutic agents. Typically, such devices provide therapy continuously or periodically according to programmed parameters. The programmed parameters can specify a therapeutic regimen (e.g., the rate, quantity, and timing of medicament delivery to a patient), as well as other functions of the medical device.

Implantable medical devices such as drug pumps are typically implanted at a location within the body of a patient (typically a subcutaneous region in the lower abdomen) and are configured to deliver a therapeutic fluid through a catheter to a target treatment site. Drug pumps typically include a drug reservoir and pumping mechanism that deliver a fluid containing a pharmaceutical agent to the patient via a catheter under a set schedule over an extended period of time to the target treatment site. The catheter used in these devices is generally configured as a flexible tube with a lumen running the length of the catheter that transports the therapeutic fluid.

Implantable medical devices can have refillable drug reservoirs for housing therapeutic fluids that are periodically refilled so that the implanted device can be employed for chronic long-term use. A refill apparatus or needle can be percutaneously inserted into an access port of the device that is in communication with the drug reservoir to provide fresh therapeutic fluid. Ascertaining the current volume capacity of the drug reservoir, e.g., the relative fullness, may be useful during refill procedures or for determining whether the device is functioning properly. However, accurately determining the current volume capacity of the drug reservoir may be challenging and may often require labor or time intensive methods. For example, during refill, the residual supply of therapeutic fluid in a drug reservoir may be determined by evacuating, or aspirating, to the extent possible, the residual supply of therapeutic fluid in the reservoir using a syringe, and determining the volume of the remaining therapeutic fluid from the graduations on the syringe. Such procedure may be described as being wasteful and invasive for the patient.

In some conventional systems, the present volume level within a drug reservoir is estimated based on the number of cycles implemented by the pumping mechanism of the device. Under a scheduled regimen, the device may be configured to pump or deliver a select amount of fluid from the drug reservoir to the target treatment site. The system is thus programmed to deliver a select amount of therapeutic fluid to the patient with each cycle of the pump mechanism. Knowing the number of cycles that the pump mechanism undergoes provides an estimate of the fluid delivered to the patient and, in turn, an estimate of the current volume capacity of the drug reservoir. However, pressure differentials within the system created by, for example, restrictions within a catheter, variations induced by the pumping mechanism, leaks within the system, and similar complications are generally not accounted for with such mechanisms. Thus, the difference between the actual amount of fluid remaining within the drug reservoir and the anticipated amount remaining may be substantially different. Further, such accounting mechanisms fail to analyze the amount of fluid introduced during a refill procedure.

SUMMARY

Embodiments of the present disclosure provide a system and method for accurately measuring the current reservoir volume capacity of an implantable medical device. The disclosed systems use an ultrasound or infrared transmitter and one or more corresponding sensors mounted at different positions relative to the sides of the drug reservoir of the implantable medical device. As the volume of the drug reservoir changes the travel path of the signal transmitted from the ultrasound or infrared transmitter to the corresponding sensors changes. Monitoring the change in travel path can be used to determine the current volume capacity of the drug reservoir (e.g., the relative fullness of the drug reservoir). In some embodiments, the signal may be transmitted towards a side of the drug reservoir at an acute angle (e.g., angle less than 90 degrees) relative to the side so that the relative location for the signal reception changes as the drug reservoir volume changes allowing for the sensor to be positioned to selectively receive the transmitted signal depending on the current volume capacity of the drug reservoir.

In an embodiment, the disclosure describes an implantable medical device including a housing defining a reservoir chamber therein; a drug reservoir located within the reservoir chamber of the housing, the drug reservoir having a first side and a second side directly opposite the first side defining a reservoir volume there between; and a volume sensor system including an ultrasound transmitter within the reservoir chamber and positioned to transmit an ultrasound signal toward the second side of the drug reservoir at an acute angle relative to the second side, and a plurality of ultrasound sensors adjacent to at least one of the first side or second side of the drug reservoir, where the plurality of ultrasound sensors are positioned to selectively receive the signal from the transmitter at different reservoir volume levels to indicate a current volume capacity of the drug reservoir.

In another embodiment, the disclosure describes an implantable medical device including a housing defining a reservoir chamber therein; a drug reservoir located within the reservoir chamber within the housing, the drug reservoir having a first side and a second side directly opposite the first side defining a reservoir volume there between; and a volume sensor system including an ultrasound transmitter positioned to transmit an ultrasound signal toward the second side of the drug reservoir, and an ultrasound sensor adjacent mounted directly adjacent to the second side of the drug reservoir and configured to receive the ultrasound signal from the ultrasound transmitter to determine a current volume capacity of the drug reservoir based on a travel distance of the ultrasound signal.

In another embodiment, the disclosure describes a method of determining a reservoir volume capacity of an implantable medical device. The method includes transmitting an ultrasound signal using a volume sensor system of the implantable medical device, where the implantable medical device includes a housing defining a reservoir chamber therein and a drug reservoir located within the reservoir chamber, the drug reservoir having a first side and a second side directly opposite the first side defining the reservoir volume there between, where a volume sensor system includes an ultrasound transmitter and a plurality of ultrasound sensors within the reservoir chamber, where the ultrasound transmitter is positioned to transmit the ultrasound signal toward the second side of the drug reservoir at an acute angle relative to the second side; and receiving the ultrasound signal using a sensor of the plurality of ultrasound sensors positioned adjacent to the first side or the second side of the drug reservoir, where changes to the reservoir volume alters a signal path of the ultrasound signal so that plurality of ultrasound sensors selectively receive the signal from the transmitter at different reservoir volume levels to indicate a current volume capacity of the drug reservoir.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which.

Figure 1:
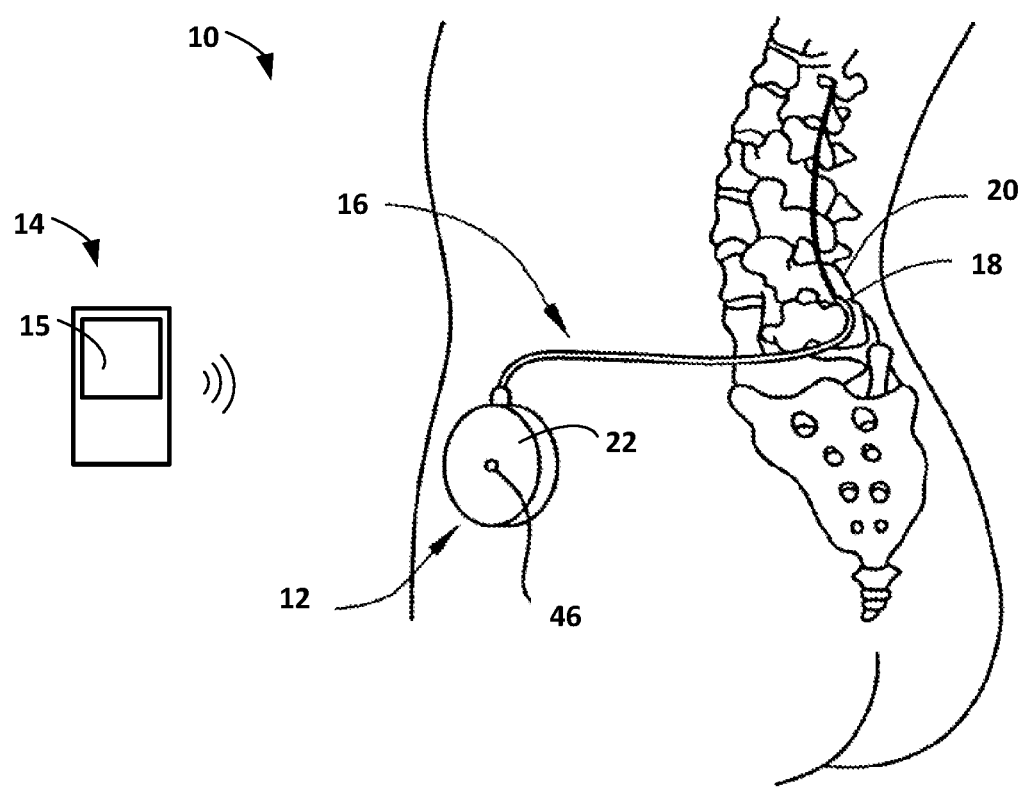
FIG. 1 is schematic view showing an exemplary drug infusion system including an external device and an implantable medical device containing the disclosed volume sensor system implanted in a patient.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 is schematic view showing an exemplary drug infusion system 10 including an implantable medical device 12 illustrated as an implantable drug pump implanted in a patient and an external device 14 configured to wirelessly communicate with implanted medical device 12. Infusion system 10 also includes catheter 16, which may include an elastomeric tube, coupled to implantable medical device 12 and configured to transport a therapeutic fluid from implantable medical device 12 to a target treatment site 18 under a set drug regimen established by the processing circuitry of implantable medical device 12.

Implantable medical device 12 may be surgically implanted in any suitable location, such as subcutaneously in the pectoral, abdominal, or other region of the body of the patient. The target treatment site 18 may be any suitable location within the body of the patient such as within the intrathecal space along the spinal canal 20 of the patient as shown in FIG. 1, the blood stream, the stomach, the cranium, the heart, or other suitable location.

As discussed further below, implantable medical device 12 may include processing circuitry configured to wirelessly communicate with external device 14 to allow for monitoring or adjustments to the programing of implantable medical device 12 as well as assessment of the current volume capacity of the drug reservoir within implantable medical device 12.

External device 14 may include a display 15 for presenting information to a user, such as a healthcare provider or a patient. In one or more embodiments, external device 14 is capable of presenting volume information, using the display 15 or another output device, to the user regarding the current volume capacity of the therapeutic fluid remaining or located within the drug reservoir of implantable medical device 12 and other useful information. In some embodiments, external device 14 may be capable of presenting alerts, or notifications via display 15 or another output device to indicate to the user that the current volume capacity of the therapeutic fluid within the drug reservoir of implantable medical device 12 has reached a particular capacity or threshold value. For example, the external device 14 may provide any alert, or notification, to a user when the drug reservoir contains less than a threshold volume of prescribed therapeutic fluid (e.g., less than 10% total capacity or some other value), a threshold number of remaining therapeutic doses, or a threshold duration of remaining therapeutic doses (e.g., less than a week left of prescribed doses of the therapeutic fluid or other duration).

Any suitable external device 14, such as a programmer (e.g., a MEDTRONIC, INC. N'VISION clinician programmer or a MEDTRONIC, INC. MYP™ patient programmer), a tablet computer, a smart phone, a personal data assistant, a laptop computer, or the like, may be employed, provided that it can communicate with implantable medical device 12. In some embodiments external device 14 may include a cellular telephone, tablet, or desktop computer with an associated monitor serving as display 15. In order for a person to interact with external device 14, external device 14 may include a user interface coupled to the computing apparatus. The user interface may include a touchscreen, a keyboard, graphical user interface, and/or combinations thereof. For example, display 15 may be touchscreen that may allow a user to view and/or manipulate data on display 15 and allow a user to interact with implantable medical device 12. External device 14 may further include a speaker for broadcasting audible tones or messages used to communicate with a user regarding, e.g., vocalizations of volumes, alerts, alarms, notifications, etc. External device 14 may further include a communications module or other functionality used for transferring data (e.g., over the internet, over a network, etc.) to a central database or communicating with patient management systems.

External device 14 may be a microprocessor-controlled device, and thus, may include computing apparatus that includes one or more microprocessors that operate with associated memory for controlling various processes and functions of external device 14 including initiating one or more volume measurements using implantable medical device 12, wirelessly transferring data and commands between implantable medical device 12 and external device 14, issuing alerts, or notifications based on the current volume capacity of the drug reservoir of implantable medical device 12, calculating a current volume capacity of the drug reservoir of implantable medical device 12 based on the signals transmitted and relieved between the disclosed transmitters and sensors of implantable medical device 12, and the like. Still further, external device 14 may be further configured to store data from implantable medical device 12 such as, the drug reservoir volume data over time, average flow rates, sensor system diagnostics, volume discrepancies (e.g. with respect to programmed expectations) for various time durations, events where volume changes exceed selected thresholds, etc.

External device 14 may include a telemetry circuit and an antenna for bidirectional communication with implantable medical device 12. Data and commands may be transmitted and received during uplink or downlink telemetry between implantable medical device 12 and external device 14 using the telemetry circuit and the antenna. The wireless operable coupling between implantable medical device 12 and external device 14 may use one or more wireless (e.g., radio frequency) data transmission protocols such as, e.g., BLUETOOTH, WI-FI, Medical Implant Communications Service (MICS), any protocol in the ultra-high frequency (UHF) band, any protocol in the super high frequency (SHF) band, low frequencies, etc.

Figure 2:
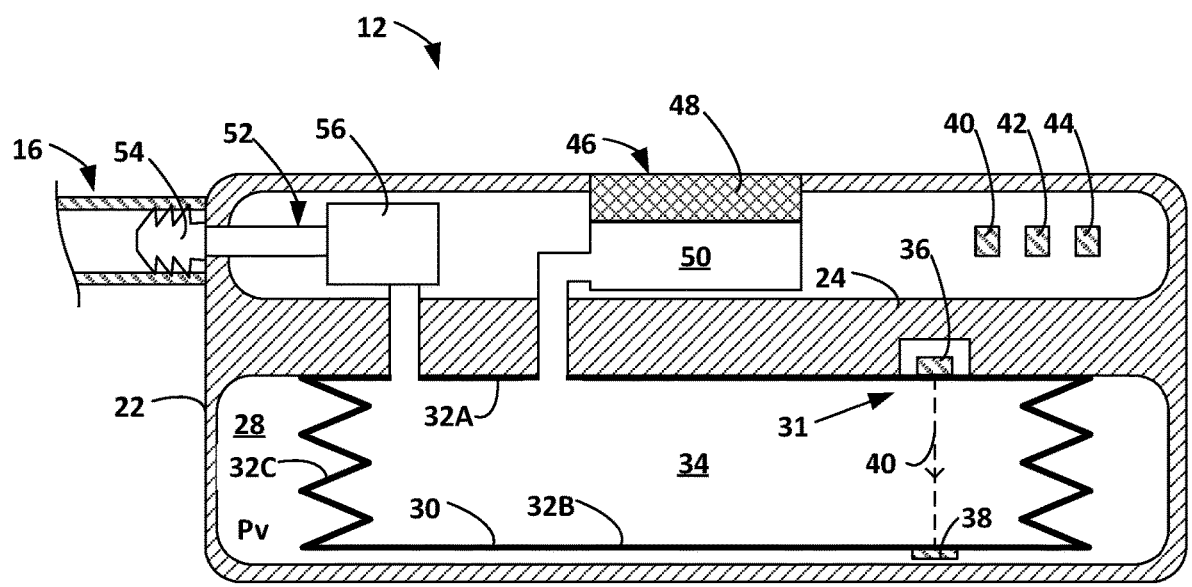
FIG. 2 is a schematic cross-sectional view of an exemplary implantable medical device such as the one shown in FIG. 1 including volume sensor system having an ultrasound transmitter and an ultrasound sensor.

FIG. 2 is a schematic cross-sectional view of an example implantable medical device 12 that may be used with system 10 in FIG. 1 illustrating select internal features of the device. Although device 12 is generally described herein in relation to an implantable drug pump, the disclosed volume sensor systems of the present disclosure may be utilized with other types of drug delivery devices such as ambulatory or wearable infusion pumps. As shown in FIG. 2, implantable medical device 12 includes a housing 22 with a bulkhead 24 that divides an interior space of housing 22 into two or more chambers. The interior space of housing 22 includes a reservoir chamber 28 that is at least partially defined by bulkhead 24. Reservoir chamber 28 contains expandable drug reservoir 30 that receives the therapeutic fluid, which is then administered to the patient under a set drug regimen. Bulkhead 24 may help also separate or hermetically seal drug reservoir chamber 28 and expandable drug reservoir 30 from other components contained in implantable medical device 12. Although certain examples are described with respect to expandable drug reservoir 30, in other examples, the reservoir may not be expandable.

Expandable drug reservoir 30 includes a first side 32A and second side 32B different than first side 32A. In some examples, second side 32B is directly opposite first side 32A. The perimeter of expandable drug reservoir 30 includes collapsible side 32C to create an enclosed space containing reservoir volume 34. The designation of "first," "second," or "third" side is used to differentiate the walls of drug reservoir 30 and is not intended to imply a specific orientation or total number of sides within implantable medical device 12. Therefore, while first side 32A is depicted in FIG. 2 as being directly adjacent to bulkhead 24, it will be understood that either first or second sides 32A or 32B may be adjacent to bulkhead 24. Additionally, or alternatively, collapsible side 32C, or at least a portion thereof, may be positioned directly adjacent to bulkhead 24 with first and second sides 32A and 32B aligned perpendicular thereto.

In some embodiments, first and second sides 32A and 32B of drug reservoir 30 may be described as rigid, or resilient, so as to be resistant to deflection. For example, in this embodiment, second side 32B may lie in plane, or be planar, and may resist deflection out of the plane and move as a single element, e.g., towards and away from bulkhead 24. More specifically, second side 32B may be described as moving substantially linearly along an axis that is perpendicular to the plane of the side. In other words, second side 32B may be described as moving orthogonally to the plane that second side 32B lies within.

In some embodiments, device may include a guide mechanism used in conjunction with drug reservoir 30 to maintain proper alignment of second side 32B as it transitions form full to a depleted configuration. The guide mechanism can also help ensure proper alignment of volume sensor system 31 through the full range of movement of second side 32B.

Expandable drug reservoir 30 expands from a depleted configuration to a full configuration based on the receipt and amount of therapeutic fluid introduced into reservoir volume 34. In some embodiments, collapsible side 32C of expandable drug reservoir 30 may be a collapsible bellows-style cylindrical side wall that allows at least one of first or second side 32A or 32B to move with the change of volume. When in the full configuration, first side 32A and second side 32B will be at a maximum separation distance from each other. In contrast, in the depleted configuration, first side 32A and second side 32B will be at a minimum separation distance from each other. In the illustration shown in FIG. 2, first side 32A is positioned and attached to bulkhead 24 allowing second side 32B to move substantially parallel (e.g., parallel or nearly parallel) to first side 32A with changing therapeutic fluid volume. It will be understood, however, that drug reservoirs other than bellows-type reservoirs may be employed using the exemplary systems, apparatus, devices, and methods described herein.

Drug reservoir 30 may be constructed of any suitable material. In some embodiments, sides 32A-32C of drug reservoir 30 may be made of a nonferromagnetic metal such as titanium, a rigid polymeric material such as parylene, or the like. In some embodiments, drug reservoir 30 may be a bellows-style titanium drug reservoir.

In some embodiments, reservoir chamber 28 may further include a propellant, or propellant mixture, Pv disposed outside of drug reservoir 30 and reservoir volume 34 but inside housing 22 so as to at least partially surround drug reservoir 30. The propellant Pv can exert a pressure on at least a portion of expandable drug reservoir 30 such that the pressure reservoir volume 34 is positive. Further, when therapeutic fluid is removed from drug reservoir 30 (e.g., to delivered to the patient, to be removed from the pump by a clinician, etc.), the pressure exerted on drug reservoir 30 by the propellant Pv may assist in fluid exiting from device 12. More specifically, drug reservoir 30 may contract due to the therapeutic fluid exiting from drug reservoir 30 and the pressure exerted on the exterior of drug reservoir 30 by the propellant Pv.

During refill procedures or the general administration of therapeutic fluid from implantable medical device 12 it may be important to accurately know the amount of therapeutic fluid contained within expandable drug reservoir 30. Tracking of the volume capacity (e.g., the relative fullness of drug reservoir 30) may be important to understand if any leaks or occlusions within the infusion system 10 have occurred, whether device 12 is malfunctioning, whether proper refilling of device 12 has occurred, as well as a number of other properties of the device.

The disclosed implantable medical device 12 provides a mechanism for accurately determining the current volume capacity of drug reservoir 30 by using a volume sensor system 31 that includes an ultrasound transmitter 36 and an ultrasound sensors 38 configured to detect the relative change in position between first side 32A and second side 32B to provide an accurate assessment of the current volume capacity of drug reservoir 30. For example, as the internal reservoir volume 34 of drug reservoir 30 changes with the increase or decrease of therapeutic fluid contained therein, the relative distance between first side 32A and 32B will change. Measuring the distance between first side and second side 32A and 32B provides a useful value to determine the current volume capacity of drug reservoir 30.

Ultrasound transmitter 36 operates in conjunction with discrete ultrasound sensor 38, which are each mounted on opposite sides 32A and 32B of drug reservoir 30. In FIG. 2, ultrasound transmitter 36 is depicted as being mounted adjacent to first side 32A and ultrasound sensor 38 is depicted as being mounted adjacent to second side 32B. Transmitter 36 directs an ultrasound signal 40 from first sidewall 32A toward second sidewall 32B substantially orthogonal to second side 32B such that the location for interception of signal 40 on second side 32B will remain relatively fixed regardless of the current volume of drug reservoir 30. Ultrasound transmitter 36 and receiver 38 may be used to determine the time of travel of signal 40 through the therapeutic fluid contained within drug reservoir 30, thereby allowing for the determination of the relative distance between the inner surfaces of first side 32A and second side 32B and in turn the current volume capacity of drug reservoir 30.

By using an ultrasound transmitter 36 and sensor 38 mounted at different relative positions adjacent to drug reservoir 30 as opposed to a single unit transmitter and receiver, the disclosed volume sensor may provide more accurate results in determining the current volume capacity of drug reservoir 30. For example, with a single unit transmitter/receiver mounted in the position of transmitter 36, detection of the signal would rely on reflection of the signal off second side 32B. Such a system will have inherent latency between the time when the transmitter/receiver is transitioned between a transmit mode and a receive mode. As the relative distance between first side 32A and second side 32B decreases with decreasing volume, the duration between signal transmission and detection will likewise decrease leading to potential inaccuracies in measuring the transmission duration of low volume capacities. Separating the transmitter and sensor as is shown in FIG. 2 may eliminate some of the technical issues and provide more accurate measurement of the distance between first side 32A and second side 32B even at low volume levels.

Transmitter 36 and sensor 38 may be initially calibrated or normalized prior to or after implantation to the patient. For example, the relative distance as measured between transmitter 36 and sensor 38 may be plotted against known volume levels of drug reservoir 30 to provide a determination of volume capacity as a function of relative distance between first and second sides 32A and 32B. In some embodiments, the characteristics of the therapeutic fluid (e.g., density of the fluid, the physical properties of the drug material or fluid carrier, and the like) may affect the speed of travel of signal 40 through reservoir volume 34. Thus, it may be beneficial to calibrate the volume sensor of device 12 with a fluid substantially the same (e.g., the same or nearly the same) as the therapeutic fluid intended during actual use of infusion system 10 to ensure accurate measurements.

Implantable medical device 12 also includes other components such as processing circuitry 40, telemetry circuit 42, and power source 44 to power and control the various components implantable medical device 12. Processing circuitry 40 may include one or more microprocessors that operate with associated memory for controlling various processes and functions of the implantable medical device 12 including the various components of volume sensor system 31 and pump mechanism 56. Telemetry circuitry 42 may include an antenna, and may be configured to be used with processing circuitry 40 to transmit and receive data and commands during uplink or downlink telemetry between device 12 and external device 14 to provide wireless operable coupling between implantable medical device 12 and external device 14 via suitable wireless data transmission protocols such as, e.g., BLUETOOTH, WI-FI, Medical Implant Communications Service (MICS), any protocol in the ultra-high frequency (UHF) band, any protocol in the super high frequency (SHF) band, low frequencies, etc.

Implantable medical device 12 further includes an access port 46 through which a needle of a refill kit, may enter to refill drug reservoir 30. Access port 46 may include a self-sealing, needle-penetrable septum 48 to allow access to refill chamber 50 that is in fluid communication with reservoir volume 34 of drug reservoir 30. While not shown in FIG. 2, access port 46 may include other useful features such as a prefilter, flow valves, or other components that may be useful in such systems.

Implantable medical device also includes outlet port 52 in fluid communication with reservoir volume 34 of drug reservoir 30. Outlet port 52 may include a suitable catheter connector 54 such as a barb-style connector configured to couple with the proximal end of treatment catheter 16 during an implantation procedure. Implantable medical device 12 may also include, or contain, a catheter access port in communication with catheter 16 at a location downstream of drug reservoir 30 for sampling fluid.

Implantable medical device 12 may include any suitable pumping mechanism 56 or structure capable of delivering one or more fluids from drug reservoir 30 to target treatment site 18 under a scheduled regimen. In some embodiments pumping mechanism 56 may be powered by power source 44 and processing circuitry 40 (e.g., piston pumps, diaphragm pumps, peristaltic pumps, etc.), may be activated based on pressure to drive fluid out of drug reservoir 30 (e.g., using collapsing diaphragms, expanding bladders, osmotic, pressurized propellant, etc.), or combinations thereof.

In some embodiments, operation of pumping mechanism 56 may be controlled and monitored by processing circuitry 40 to track the cycles undergone by pumping mechanism 56 during operation to determine an anticipated volume capacity of drug reservoir 30 at any given point in time. The anticipated volume capacity can then be compared to current volume capacity provided by volume sensor system 31 to provide useful information regarding the function of system 10. For example, relative consistency between the two determinations (e.g., anticipated vs current volume capacity) may indicate normal operation of system 10. However, if the anticipated volume capacity is lower than the current volume capacity determined by volume sensor system 31, system 10 may indicate to the user that a higher level of therapeutic fluid remains in drug reservoir 30 than anticipated, which may be an indication of possible occlusion somewhere within system 10. Likewise, if the anticipated volume capacity is higher than the current volume capacity determined by volume sensor system 31, system 10 may indicate to the user that a lower level of therapeutic fluid remains in drug reservoir 30 than anticipated, which may be an indication of possible leaks or other malfunctions within system 10. In either scenario, implantable medical device 12 may send a signal to external device 14 to alert the user of possible complications with system 10.

The sampling rate of volume sensor 31 may set to balance power usage and activity demands. For example, in situations that require a higher rate of sampling, e.g., during refill procedures, volume sensor system 31 may be set to transmit and receive signal 106 on the order of every second to monitor the filling process. During routine operation, a lower rate of sampling may be used, on the order of hourly, daily, or the like to preserve battery life while also provided useful feedback regarding the current volume capacity of drug reservoir 30. Additionally, or alternatively, the sampling rate may coincide with the drug delivery rate. For example, systems with higher drug delivery rates may sample more often compared to systems with lower drug delivery rates.

Figure 3A:
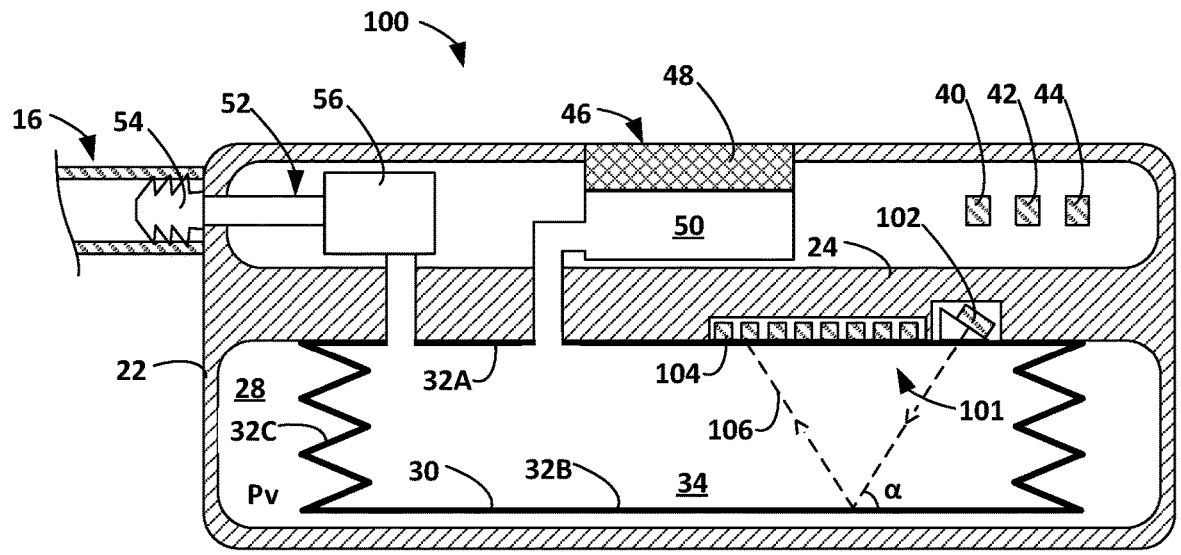
FIGS. 3A and 3B are schematic cross-sectional views of another exemplary implantable medical device such as the one shown in FIG. 1 including volume sensor system having an ultrasound transmitter and a plurality of ultrasound sensors showing a drug reservoir in a near full configuration (FIG. 3A) and a near depleted configuration (FIG. 3B).
Figure 3B:
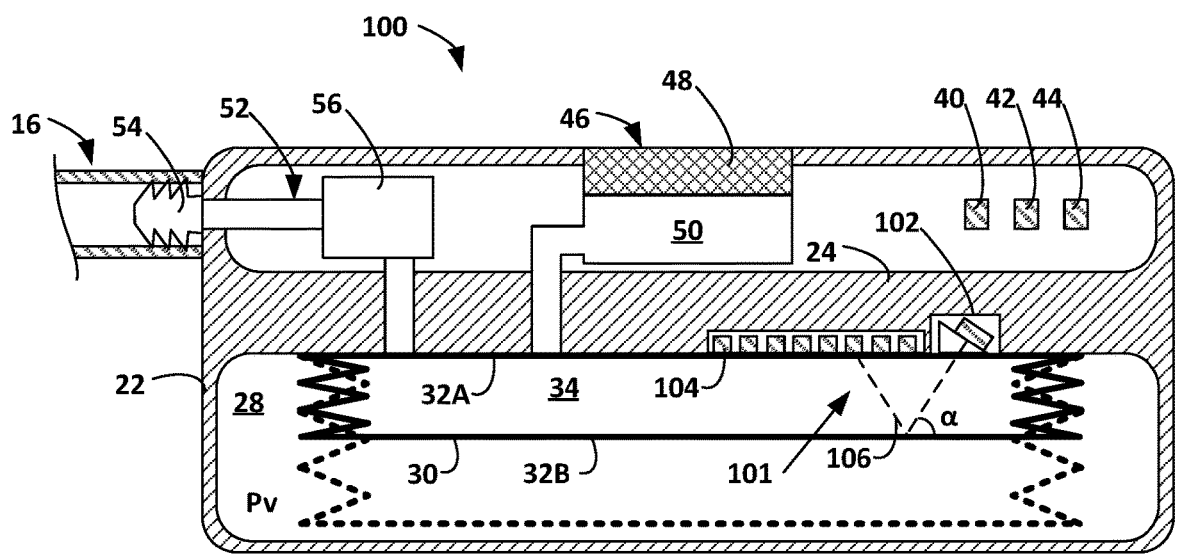

FIGS. 3A and 3B are schematic cross-sectional views of another example implantable medical device 100 that may be used with infusion system 10 of FIG. 1. Components of the disclosed implantable medical devices sharing the same numerical indicators may be substantially the same as those described above and will not be repeated for simplicity.

FIGS. 3A and 3B illustrate an alternative volume sensor system 101 design that includes an ultrasound transmitter 102 and a plurality of ultrasound sensors 104. FIG. 3A illustrates drug reservoir 30 in a near-full configuration while FIG. 3B illustrates drug reservoir 30 in a more depleted configuration. As shown in FIGS. 3A and 3B, transmitter 102 is positioned adjacent to first side 32A of drug reservoir 30 and configured to transmit signal 106 from first side 32A toward second side 32B at an acute angle (a) such that signal 106 is selectively received by one of sensors 104 depending on the current volume capacity of drug reservoir 30. For example, as drug reservoir 30 transitions from a substantially full configuration (FIG. 3A) to a more depleted configuration (FIG. 3B), the relative distance between first side 32A and second side 32B will decrease. Due to acute angle (a), the intercept location of signal 106 will likewise change as the relative distance between first side 32A and second side 32B changes. This change in intercept location allows for sensors 104 to be positioned at different locations along the intercept path of signal 106 which provides a direct indication of the relative distance between first side 32A and second side 32B. For example, a first sensor 104 may be positioned to intercept signal 106 when the second side 32B is at the minimal separation distance from first side 32A representing a depleted state. Similarly a second sensor 104 may be positioned to intercept signal 106 when second side 32B is a the maximum separation distance from first side 32A representing a full configuration. Additional sensors 104 may be positioned at locations there between to intercept signal 106 at various stages through the travel path from full to depleted states. Depending on which sensor 104 intercepts signal 106 will indicated the relative positioning of second side 32B to first side 32A which may then be used to indicate the current volume capacity of drug reservoir 30.

The volume sensor system 101 provides certain advantages in that the system does not require an accurate determination of the travel speed or distance of signal 106 through the fluid filling volume reservoir 34 and instead relies on the geometric configuration of drug reservoir 30. Thus, changes in the characteristics of the therapeutic fluid (e.g., fluid density, drug composition, fluid carrier, and the like) will have little to no effect on the determination of the current volume capacity when using volume sensor system 101 thereby providing a more robust and reliable system.

The selection of acute angle ($\alpha$), the total number of sensors 104, and the positioning of sensors 104, may depend on the relative size of sensors 104, the intended precision of volume sensor system 101, change in separation distance of first and second sides 32A and 32B between full and depleted configurations, and similar factors. For example, typical ultrasound sensors may have an intercept surface cross section of about 1 millimeters (mm) to about 5 mm. In a system containing N total sensors 104 configured to detect different configurations from full to depleted volume capacity, the sensors may be linearly aligned along the intercept path of signal 106 and $\alpha$ may be approximated using conventional geometry incorporating the change in separation distance of first and second sides 32A and 32B between full and depleted configurations and the total intercept surface cross section for all N sensors. In some embodiments, a suitable a may be between about 10 degrees and about 85 degrees, more preferably between about 30 degrees and about 70 degrees.

In some embodiments, signal 106 may undergo dispersion as the signal propagates through the therapeutic fluid towards sensors 104. Such dispersion may cause multiple sensors 104 to intercept a given signal 106. Additionally, unintended reflections of signal 106 within drug reservoir 30 may likewise occur leading to detection of signal 106 by more than one sensor 104. To account for such dispersions, processing circuitry 40 may analyze the relative strength and timing of the received signals by sensors 104 to determine where interception of signal 106 presents the highest amplitude and first incidence (e.g., first in time) to determine the current volume capacity of drug reservoir 30.

While plurality of sensors 104 are depicted adjacent to first side 32A in FIGS. 3A and 3B, in other embodiments, sensors 104 may be positioned adjacent to second side 32B with transmitter adjacent to first side 32A or vice versa. Alternatively, sensors 104 may be positioned adjacent to both first and second sides 32A and 32B. Such configurations may allow for improved precision or redundancy such that signal 106 is received by more than one sensor 104 on each side 32A and 32B for a specific volume capacity.

To obtain a desired acute angle ($\alpha$), ultrasound transmitter 102 may be coupled to a ramp structure 108 that provides the desired entry angle for signal 106 toward second side 32B. In some embodiments, ramp structure 108 may be constructed integrally with first side 32A of drug reservoir 30. Alternatively, ramp structure 108 may be constructed separately from drug reservoir 30 and mechanically coupled thereto using an appropriate adhesive of comparable hardness. In embodiments where signal 106 is passed through ramp structure 108, the material used to form first side 32A and ramp structure 108 should have similar hardness and ultrasonic transmissive properties so that signal 106 is not degraded or deflected as it passes through ramp structure 108. Suitable materials for constructing ramp structure 108 may include poly(methyl methacrylate) (e.g., plexiglass), polystyrene (e.g., Rexolite® available from C-LEC Plastics, Inc), or other polymeric material.

Figure 4:
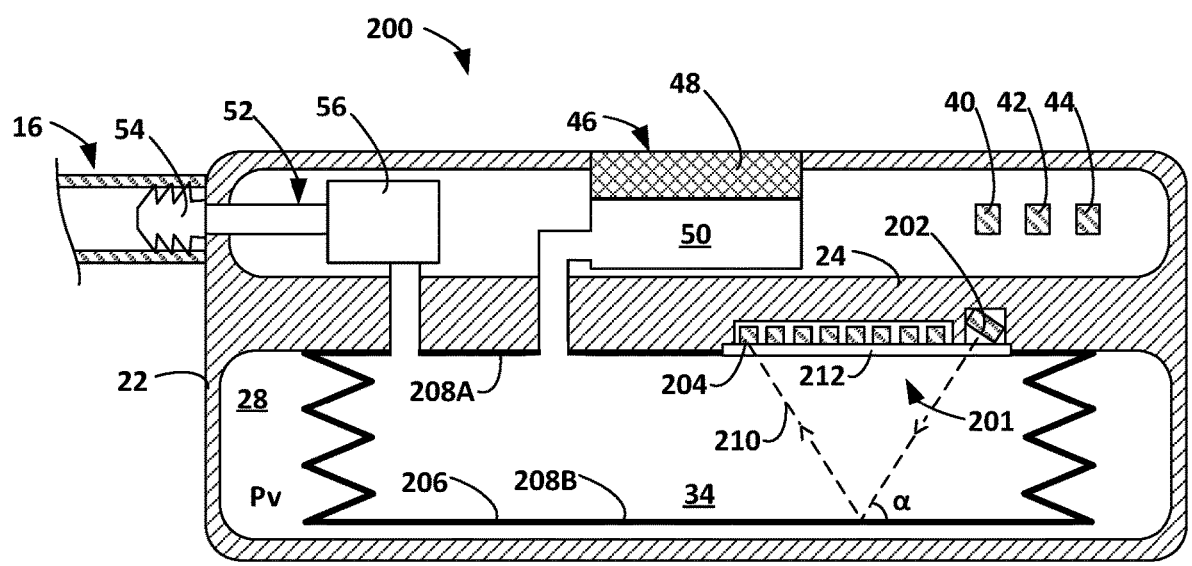
FIG. 4 is a schematic cross-sectional view of another exemplary implantable medical device such as the one shown in FIG. 1 including volume sensor system having an optical transmitter and a plurality of optical sensors.

FIG. 4 illustrates another implantable medical device 200 that includes volume sensor 201 which may be used with infusion system 10 of FIG. 1. Volume sensor system 201 includes an optical transmitter 202 and a plurality of optical sensors 204. Transmitter 202 is positioned adjacent to first side 208A of drug reservoir 206 and configured to transmit signal 210 from first side 208A toward second side 208B at an acute angle ($\alpha$) such that signal 206 is selectively received by one or sensors 204 which will depend on the current volume capacity of drug reservoir 206.

Drug reservoir 206 includes optical transmissive layer 212 along first side 208A to allow signal 210 to be transmitted from transmitter 202 through optical transmissive layer 212, reflect off second side 208B, pass back through transmissive layer 212, and be received by optical sensors 204. As drug reservoir 206 transitions from a substantially full configuration to a depleted state the travel path of optical signal 210 changes due to acute angle ($\alpha$), thereby causing signal 210 to be selectively received by one of sensors 204 depending on the current volume capacity of drug reservoir 206.

Optical transmitter 202 and sensors 204 may include an infrared or light-based emitter/detector, including by not limited to use of light emitting diode (LED), IR-LED, or other suitable device. In some embodiments, optical transmitter 202 may be configured to generate optical signal 206 having one or more wavelengths between about 350 nanometers (nm) and about 50,000 nm. Further, volume sensor system 201 should be positioned and calibrated using a fluid having optical properties (e.g., index of refraction) similar to that of the target therapeutic fluid to accurately predict the optical pathway of signal 206 through the fluid.

Figure 5:
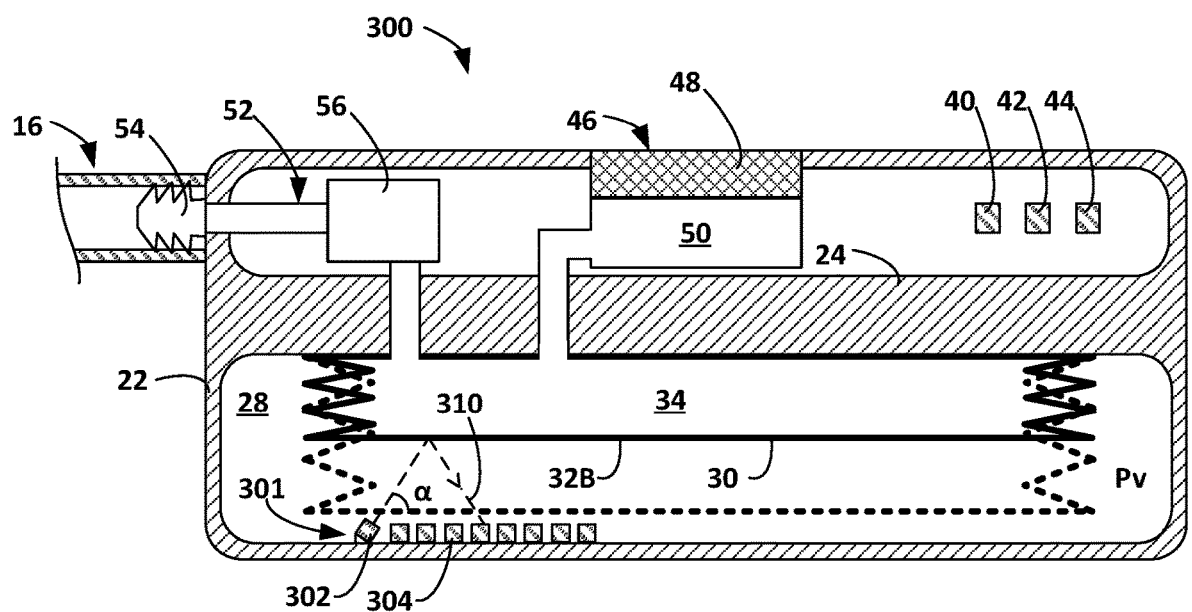
FIG. 5 is a schematic cross-sectional view of another exemplary implantable medical device such as the one shown in FIG. 1 including volume sensor system having an ultrasound or optical transmitter and a plurality of corresponding sensors.

FIG. 5 illustrates another volume sensor system 301 within implantable device 300. Volume sensor system 301 includes transmitter 302 and a plurality of sensors 304 mounted within reservoir chamber 28 adjacent to second side 32B of drug reservoir 30. Transmitter 302 sends signal 310 toward second side 32B at acute angle ($\alpha$) where signal 310 is reflected and transmitted toward sensors 304. Signal 310 is selectively received by sensors 304 depending on the current volume capacity of drug reservoir 30. Transmitter 302 and sensors 304 may operate substantially similar to ultrasound transmitter 102 and sensors 104 or optical transmitter 202 and sensors 204, but permits signal 310 to be passed through propellant Pv rather than the therapeutic fluid. As propellant Pv remains unchanged throughout the life of device 300, volume sensor system 301 may be easily calibrated at the point of manufacture and does not rely on the properties of the therapeutic fluid. Further, in situations where transmitter 302 and sensors 304 include an optical transmitter/sensor, drug reservoir 30 does not require the presence of a transmissive layer 108 to function and thus will not introduce materials that might interact and affect the stability characteristics of the therapeutic fluid contained in drug reservoir 30. Stated another way, volume sensor system 300 offers advantages over volume sensor system 201 by reducing the number of different component materials brought into contact with the therapeutic fluid.

Figure 6:
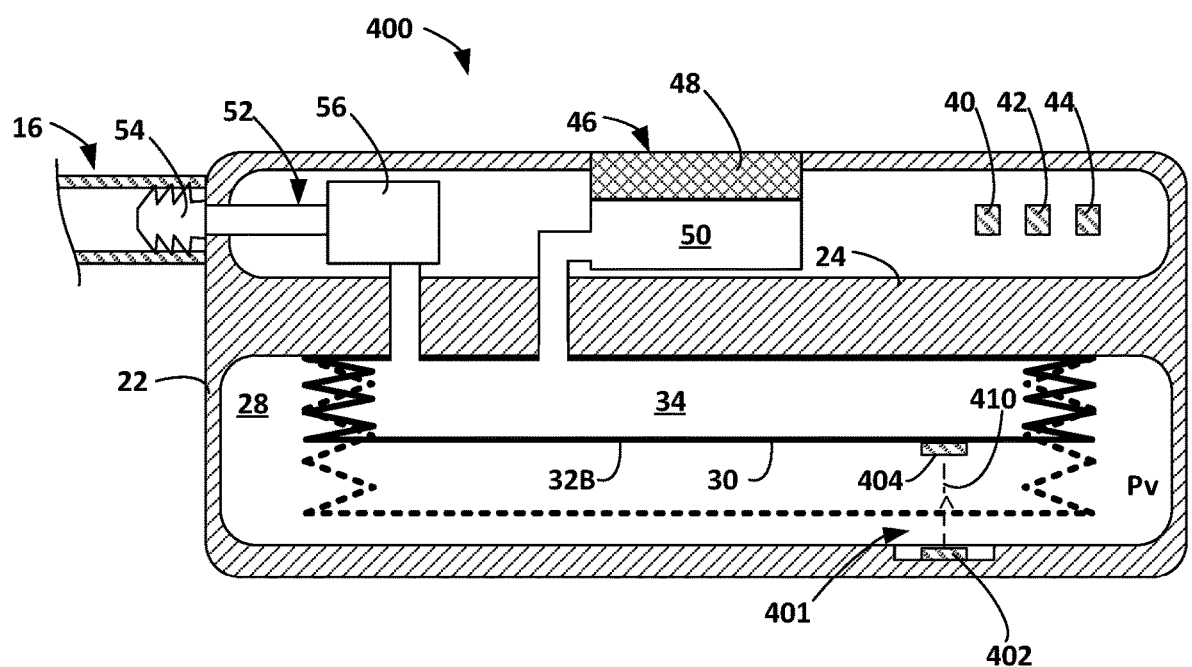
FIG. 6 is a schematic cross-sectional view of another exemplary implantable medical device such as the one shown in FIG. 1 including volume sensor system having an ultrasound or optical transmitter and a corresponding sensor.

FIG. 6 illustrates another implantable medical device 400 containing volume sensor system 401 that may be used with infusion system 10 of FIG. 1. Volume sensor system 401 includes transmitter 402 mounted within reservoir chamber 28 adjacent to second side 32B of drug reservoir 30 and a single sensor 404 mounted to second side 32B. In other embodiments, the relative position of transmitter 402 and sensor 404 may be switched so that transmitter 402 and mounted to second side 32B of drug reservoir 30 and a single sensor 404 is mounted within reservoir chamber 28 adjacent to second side 32B.

Transmitter 402 sends signal 410 toward second side 32B in a direction substantially perpendicular (e.g., perpendicular or nearly perpendicular) to second side 32B where the signal is received by sensor 404 to determine the current volume capacity of drug reservoir 30 based on the distance of travel of signal 410. Volume sensor 401 provides an advantage over volume sensor 31 in that signal 410 will always travel through the inert propellant gas Pv contained within reservoir chamber 28 without needing to travel through the therapeutic fluid, thereby allowing for convenient calibration of volume sensor 401 during manufacturing.

Transmitter 402 and sensor 404 may include an ultrasound transmitter and sensor or may include an optical transmitter and sensor similar to those described above. Both volume sensor systems 301 and 401 provide the benefit on not needing to pass a signal through the therapeutic fluid contained within drug reservoir 30 and thereby function substantially independent of the therapeutic fluid delivered to the patient.

Figure 7:
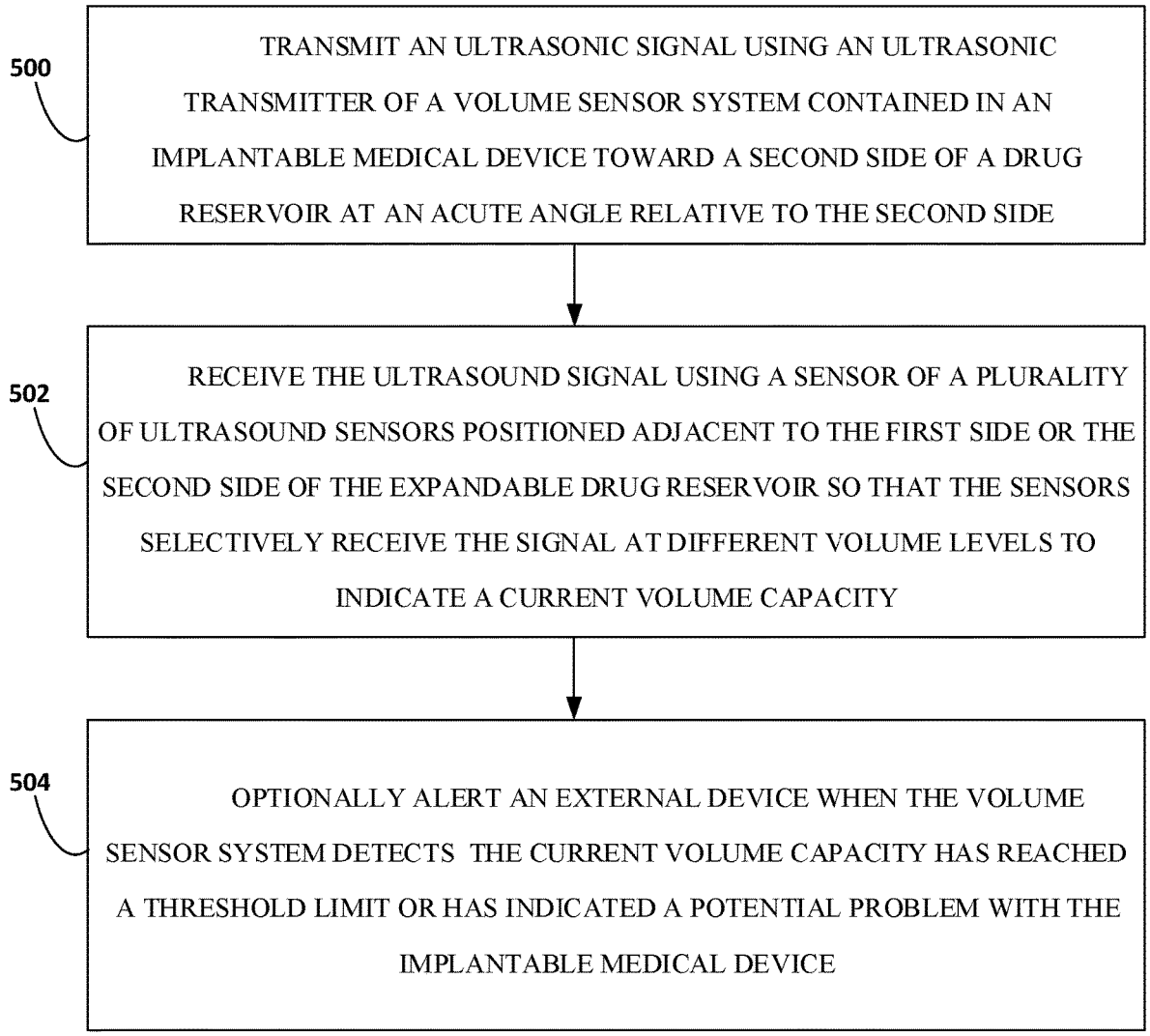
FIG. 7 is a flow diagram of a method for determining the current volume capacity of the disclosed implantable medical devices.

FIG. 7 is a flow diagram of a method determining the current volume capacity of an implantable medical device 12. For simplicity, the method of FIG. 7 is described with respect to volume sensor systems 101 of implantable medical device 100 of FIGS. 3A and 3B. However, the method may be applied or adapted for use with the other disclosed volume sensor systems described herein or the disclosed volume sensor systems may be used to preform other methods than those disclosed by FIG. 7.

The method of FIG. 7 includes transmitting ultrasound signal 106 using ultrasonic transmitter 102 toward second side 32B of expandable drug reservoir 30 at an acute angle ($\alpha$) relative to second side 32B (500) and receiving ultrasound signal 106 using a sensor of plurality of ultrasound sensors 104 positioned adjacent to first side 32A or second side 32B of expandable drug reservoir 30 such that changes to reservoir volume 34 alters a signal path of ultrasound signal 106 causing ultrasound sensors 104 to selectively receive signal 106 from transmitter 102 at different reservoir volume levels to indicate a current volume capacity of expandable drug reservoir 30 (502).

As discussed above, signal 106 may be transmitted from first side 32A toward second side 32B through the fluid contained within drug reservoir 30. Alternatively, transmitter 102 may be mounted within reservoir chamber 28 such that the ultrasound signal is transmitted through the propellant Pv contained therein rather than the therapeutic fluid contained within the drug reservoir 30 substantially similar to the system shown in FIG. 4.

The method of FIG. 7 also includes optionally alerting external device 14 when volume sensor system 101 detects the current volume capacity has reached a threshold limit or has indicated a potential problem with implantable medical device 100 (504). For example, implantable medical device 100 may be configured to alert external device 15 in response to the current volume capacity as detected by volume sensor system 101 reaching a predetermined threshold indicative of the number of therapeutic doses remaining (e.g., based on the remaining volume of the therapeutic fluid) or a duration of therapeutic doses remaining (e.g., one or more weeks remaining before device 100 become depleted). Additionally, or alternatively, implantable medical device 100 may be configured to determine an anticipated volume capacity based on operation of pumping mechanism 56 as described above, compare the anticipated volume capacity determined by pumping mechanism 56 to the current volume capacity determined by volume sensor system 101, and alert external device 14 in response to implantable medical device 100 detecting a discrepancy between the current volume capacity and the anticipated volume capacity. The discrepancy may indicate there is a potential problem with the operation of implantable medical device 100.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An implantable medical device comprising:
    a housing defining a reservoir chamber therein;
    a drug reservoir located within the reservoir chamber of the housing, the drug reservoir comprising a first side and a second side that is different from the first side defining a reservoir volume there between; and
    a volume sensor system comprising:
        an ultrasound transmitter within the reservoir chamber and positioned to transmit an ultrasound signal toward the second side of the drug reservoir at an angle relative to the second side; and
    a plurality of ultrasound sensors adjacent to at least one of the first side or second side of the drug reservoir, wherein the plurality of ultrasound sensors are positioned to selectively receive the ultrasound signal from the ultrasound transmitter at different reservoir volume levels corresponding to respective sensor positions of the plurality of ultrasounds sensors, to indicate a current volume capacity of the drug reservoir.

2. The implantable medical device of claim 1, wherein a first sensor of the plurality of ultrasound sensors is mounted directly adjacent to the first side of the drug reservoir so that the first sensor intercepts the ultrasound signal when the drug reservoir is in a full configuration.

3. The implantable medical device of claim 2, wherein a second sensor of the plurality of ultrasound sensors is mounted directly adjacent to the first side of the drug reservoir so that the second sensor intercepts the ultrasound signal when the drug reservoir is in a depleted configuration.

4. The implantable medical device of claim 1, wherein the implantable medical device is configured to send an alert to an external device in response to the current volume capacity of the drug reservoir reaching a predetermined threshold.

5. The implantable medical device of claim 4, wherein the predetermined threshold is indicative of a number of therapeutic doses remaining or a duration of therapeutic doses remaining.

6. The implantable medical device of claim 1, further comprising a pump mechanism configured to force a therapeutic fluid out of the drug reservoir under a predetermined regimen, wherein the implantable medical device is configured to send an alert to an external device in response to the implantable medical device detecting a discrepancy between the current volume capacity determined by the volume sensor system and an anticipated volume capacity determined by the pumping mechanism.

7. The implantable medical device of claim 1, wherein the ultrasound transmitter is mounted adjacent to the first side of the drug reservoir and configured to transmit the ultrasound signal from the first side to the second side of the drug reservoir.

8. The implantable medical device of claim 7, wherein at least some of the plurality of ultrasound sensors are mounted directly adjacent to the first side of the drug reservoir so that the ultrasound signal transmitted by the ultrasound transmitter is reflected off the second side of the drug reservoir.

9. The implantable medical device of claim 1, wherein at least some of the plurality of ultrasound sensors are mounted directly adjacent to the second side of the drug reservoir.

10. The implantable medical device of claim 1, wherein at least some of the plurality of ultrasound sensors are mounted at a fixed position relative to the housing adjacent to the second side of the drug reservoir.

11. The implantable medical device of claim 10, wherein the ultrasound transmitter is mounted within the reservoir chamber at a fixed position relative to the housing adjacent to the second side of the drug reservoir.

12. The implantable medical device of claim 1, further comprising a ramp structure positioned between the ultrasound transmitter and the first side of the drug reservoir to produce an acute angle of the ultrasound signal relative to the second side of the drug reservoir.

13. The implantable medical device of claim 1, wherein the acute angle is between about 30 degrees and about 70 degrees relative to a plane defined by the second side of the drug reservoir.

14. The implantable medical device of claim 1, wherein the drug reservoir is expandable.

15. The implantable medical device of claim 1, wherein the first side of the drug reservoir is directly opposite of the second side.

16. The implantable medical device of claim 1, wherein the ultrasound transmitter is positioned to transmit the ultrasound signal toward the second side of the drug reservoir at an acute angle relative to the second side.

17. A method of determining a reservoir volume capacity of an implantable medical device, the method comprising:
   transmitting an ultrasound signal using a volume sensor system of the implantable medical device, wherein the implantable medical device comprises a housing defining a reservoir chamber therein and a drug reservoir located within the reservoir chamber, the drug reservoir comprising a first side and a second side different than the first side defining the reservoir volume there between, wherein a volume sensor system comprises an ultrasound transmitter and a plurality of ultrasound sensors within the reservoir chamber, wherein the ultrasound transmitter is positioned to transmit the ultrasound signal toward the second side of the drug reservoir at an angle relative to the second side; and
   receiving the ultrasound signal using a sensor of the plurality of ultrasound sensors positioned adjacent to the first side or the second side of the drug reservoir, wherein changes to the reservoir volume alters a signal path of the ultrasound signal so that the plurality of ultrasound sensors selectively receive the ultrasound signal from the ultrasound transmitter at different reservoir volume levels corresponding to respective sensor positions of the plurality of ultrasounds sensors to indicate a current volume capacity of the drug reservoir.

18. The method of claim 17, further comprising alerting an external device in response to the current volume capacity of the drug reservoir reaching a predetermined threshold indicative of a number of therapeutic doses remaining or a duration of therapeutic doses remaining.

19. The method of claim 17, wherein the implantable medical device further comprising a pump mechanism configured to force a therapeutic fluid out of the drug reservoir under a predetermined regimen, the method further comprising:
   determining an anticipated volume capacity based on operation of the pumping mechanism, and alerting an external device in response to the implantable medical device detecting a discrepancy between the current volume capacity determined by the volume sensor system and the anticipated volume capacity determined based on operation of the pumping mechanism.

20. The method of claim 17, further comprising transitioning the drug reservoir from a full-to-depleted or a depleted-to-full configuration causing the signal path of the ultrasound signal to change and be received by different sensors of the plurality of ultrasound sensors depending on the current volume capacity of the drug reservoir.

* * * * *